United States Patent [19]

Ribier et al.

[11] Patent Number: 5,614,215
[45] Date of Patent: Mar. 25, 1997

[54] COSMETIC COMPOSITION FOR THE SIMULTANEOUS TREATMENT OF THE SURFACE AND DEEP LAYERS OF THE SKIN, ITS USE

[75] Inventors: Alain Ribier; Jean-Thierry Simonnet, both of Paris, France

[73] Assignee: L'Oreal, Paris, France

[21] Appl. No.: 366,723

[22] Filed: Dec. 30, 1994

[30] Foreign Application Priority Data

Dec. 30, 1993 [FR] France .................................. 93 15863

[51] Int. Cl.$^6$ .............................. A61K 9/127; A61K 7/00
[52] U.S. Cl. .......................... 424/450; 424/401; 514/844
[58] Field of Search ..................................... 424/450, 401, 424/59, 62, 63; 428/402.2; 514/844–848

[56] References Cited

U.S. PATENT DOCUMENTS 5,422,120  6/1995  Kim ........................................ 424/450

FOREIGN PATENT DOCUMENTS 0559502   9/1993  European Pat. Off. .
2408387   6/1979  France .
WO-A-
9315708   8/1993  WIPO .

OTHER PUBLICATIONS

Soap, Cosmetics, Chemical Specialties, vol. 69, No. 7, Jul., 1993, US p. 77 "formulation ideas" Liposome eye treatment.
International Journal of Pharmaceutics, vol. 62, No. 1, 1990, NL pp. 75–79, Gabrijelcic et al. "Evaluation of Liposomes as drug carriers into the skin by one–dimensional epr imaging".

Primary Examiner—Gollamudi S. Kishore
Attorney, Agent, or Firm—Oblon, Spivak, McClelland, Maier & Neustadt, P.C.

[57] ABSTRACT

A composition comprising a first dispersion of lipid vesicles capable of entering the deep layers of the skin and containing at least one first active substance capable of treating these deep layers, and a second dispersion of lipid vesicles capable of entering the surface layers of the skin and containing at least one second active substance, different from the first active substance, capable of treating these surface layers is found effective for anti-age, anti-wrinkle, depigmenting, nutrient, slimming, hydrating, anti-ache, anti-mycotic, anti-dermic and anti-psoriatic treatment.

16 Claims, No Drawings

COSMETIC COMPOSITION FOR THE SIMULTANEOUS TREATMENT OF THE SURFACE AND DEEP LAYERS OF THE SKIN, ITS USE

BACKGROUND OF THE INVENTION

1. Field of the Invention

The present invention relates to a composition for the cosmetic or dermatological treatment of imperfections or disorders of the skin, including the scalp. It relates more particularly to a composition of this type including at least one active substance conveyed by at least two separate types of lipid vesicles.

The invention also relates to a use of this composition for the cosmetic treatment of the skin, to the use of this composition for the preparation of an ointment intended for the dermatological treatment of the skin and to a process of cosmetic treatment of the skin.

2. Discussion of the Background

Many examples are known of cosmetic or dermatological compositions intended for the treatment of the skin, which have one or a number of active substances that are suitable for the treatment of the skin, encapsulated in lipid vesicles or spherules (also called liposomes).

Lipid vesicles or spherules are intended to mean particles made up of a membrane consisting of one or a number of concentric leaflets, these leaflets comprising one or more bimolecular layers of amphophilic lipids encapsulating an aqueous phase. The aqueous phase may contain water-soluble active substances and the bimolecular layers of amphophilic lipids may contain lipophilic active substances.

These spherules generally have a mean diameter of between 10 and 5,000 nanometres.

Among the many published documents relating to this matter, it is possible to mention French Certificate of Addition 2408387, which describes a composition based on aqueous dispersions of ionic or nonionic lipid spherules encapsulating at least one active substance. More precisely, this document describes compositions containing at least two dispersions of spherules containing different active substances, with the aim of obtaining a mixed system. That is to say, a system where a first dispersion of spherules containing a first class of active substance is used in combination with a second dispersion of spherules containing another class of active substance, which enables both categories of substances to act simultaneously at the time of the treatment and possibly to obtain a synergistic effect that would not be produced if these two classes of substances were made to act successively and separately.

The inventors have has now developed a cosmetic or dermatological composition permitting the simultaneous action of two different active substances and, furthermore, enabling these active substances to act in different regions of the skin, that is to say in the surface layers and in the deep layers of the skin, thereby very markedly enhancing the effectiveness of these compositions and the complementary or synergistic effect of the active substances used.

The inventors have also developed a cosmetic or dermatological composition enabling the same active substance to act simultaneously in the surface layers and in the deep layers of the skin, ensuring a more complete and therefore more effective treatment of the disorder from which it suffers.

Now, there are many situations in which skin disorders involve both a threat to the surface layers of the skin and accompanying change in the deeper layers of the latter.

It is well known that the skin consists of surface layers, the stratum corneum, and of deep layers, the living epidermis and the dermis. However, in the prior art it was not known to deliver such an active substance specifically into the surface layers and, simultaneously, the same or some other active substance into the deep layers.

SUMMARY OF THE INVENTION

The subject of the present invention is a cosmetic or dermatological composition for the simultaneous treatment of the surface and deep layers of the skin comprising i) a first dispersion of lipid vesicles capable of entering the deep layers of the skin and containing at least one active substance capable of treating these deep layers; and ii) a second dispersion of lipid vesicles capable of entering the surface layers of the skin and containing at least one active substance capable of treating these surface layers, wherein when said active substance contained in said first dispersion and said active substance contained in said second dispersion provide different effects, a) the vesicles of the first dispersion are not based on hydrogenated egg lecithin, cholesterol and dicetyl phosphate when the vesicles of the second dispersion are based on soya lecithin, cholesterol and dicetyl phosphate, or b) the vesicles of the first dispersion are not based on diglycerol oleate, cholesterol and dicetyl phosphate when the vesicles of the second dispersion are based on triglyceryl cetyl ether, cholesterol and dicetyl phosphate.

According to a particular embodiment, the active substances present in the first vesicle dispersion and in the second are the same.

DETAILED DESCRIPTION OF THE PREFERRED EMBODIMENTS

The Applicant has employed a means for sorting the vesicles, enabling a person skilled in the art to select easily the lipid vesicles capable of conveying the active substance into the deep layers of the skin, which are called depth vesicles, and those capable of conveying the active substance into the surface layers of the skin, called surface vesicles.

This sorting is performed on the basis of the diffusion constant D of a probe introduced into the vesicles. This probe is ASL [N-(1-oxyl-2,2,6,6-tetramethyl-4-piperidyl)-N-dimethyl-N-hydroxyethylammonium iodide] of formula:

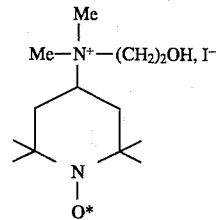

The vesicles for which the diffusion constant D of the probe in the stratum corneum is $>1\times10^{-7}$ $cm^2s^{-1}$ are the vesicles capable of entering the deep layers of skin.

The vesicles for which the diffusion constant D of the probe in the stratum corneum is $<1\times10^{-7}$ $cm^2s^{-1}$ are the vesicles capable of conveying the active substance into the surface layers of the skin.

The vesicles of the first category, called depth vesicles, are generally in a fluid state at ambient temperature (around 20° C.) and those of the second category, called surface vesicles, are generally in a gelled state at ambient temperature. The means for recognizing the state of the vesicles consists in determining the phase transition temperature (lameliar fluid-gel) of the main lipid of which their membrane consists, by differential thermal analysis (DTA).

Other characteristics of these vesicles relate to their ability to deliver the active substance more or less in depth in the skin. This is particularly the case with the encapsulation ratio.

Glucose is a marker traditionally employed for this type of determination (cf. especially "Liposomes, a practical approach" by R.R.C. New, IRL Press (1990), p. 125–136).

The encapsulation ratio is expressed as the volume of glucose solution encapsulated in the vesicles, measured in μl in relation to the unit weight (mg) of the lipids of which the membrane consists. This encapsulation ratio is determined immediately after the stage of separation of the free glucose and of the encapsulated glucose ($T_o$) and twenty four hours after this separation ($T_{24}$ hours).

The difference between these 2 successive determinations illustrates the permeability of the vesicles for the encapsulated glucose, and this can also be called their encapsulation potential.

The first category of vesicles (delivering the active substance into the deep layers of the skin) has a high potential for encapsulation of the water soluble small molecules traditionally modelled by glucose, this encapsulation potential being maintained for at least 24 hours. The second category of vesicles (delivering the active substance into the surface layers of the skin) does not retain glucose in the encapsulated state for the same time.

The main lipids constituting the vesicles of the first category (active substance delivered in depth) include at least one linear and saturated fatty chain of length ranging from 16 to 30 carbon atoms, such as hydrogenated phospholipids (from plants or from egg), saturated synthetic phospholipids such as dipalmitoylphosphatidylcholine, or the alkyl ethers or alkyl esters of polyols containing one, two or three fatty chains per molecule. These lipids are employed by themselves or mixed.

The main lipids constituting the vesicles of the second category (active substance delivered at the surface) are chosen in particular from the group including ionic lipids such as especially the plant- or egg-based natural phospholipids containing unsaturated fatty chains of 16 to 30 carbon atoms, nonionic lipids such as the alkyl ethers or alkyl esters of polyols containing one or several fatty chains per molecule, including at least one fatty chain of length shorter than 16 carbon atoms, such an lauryl polyglyceryl-6-cetearyl glycol ether, described in detail in Patent Application FR 92-09603 filed by L'Oréal.

It is possible, in a known manner, to incorporate into the lipid phase constituting the lipid membrane of the vesicles at least one additive chosen from the group consisting of sterols (phytosterols, cholesterols, polyoxyethylenated phytosterols), long-chain alcohols, diols and triols (phytanetriol), long-chain amines and their quarternary ammonium derivatives, phosphoric esters of fatty alcohols and their alkali metal salts (Na, K) such as dicetyl phosphate, sodium dicetyl phosphate, alkyl sulphates (sodium cetyl sulphate), alkali metal salts of cholesterol sulphate or of cholesterol phosphate, the sodium salt of phosphatidic acid, lipoaminoacids and their salts such as sodium acylglutamates.

As an example of vesicles of the first category (delivering the active substance into the deep layers of the skin) there may be mentioned the vesicles obtained from the following lipids (CTFA name):

A/cholesterol/casein lipoamino acid, especially in a weight ratio of 45/45/10 (where A is a triglyceryl cetyl ether marketed by the Chimex company under the name CHIMEXANE NL);

B/cholesterol/dicetyl phosphate, especially in a weight ratio of 60/35/5 (where B is a mixture of triglyceryl mono-, di- and tricetyl ethers marketed by the Chimex company under the name CHIMEXANE NT);

Span 40 (from ICI) or sorbitan palmitate/cholesterol/ sodium acylglutamate (sold by the Ajinomoto company under the name HS 11), especially in a weight ratio of 47.5/47.5/5;

PEG 8 stearate/cholesterol/sodium acylglutamate, especially with a weight ratio of 47.5/47.5/5 (where PEG 8 stearate is polyethylene glycol containing 8 ethylene oxide units marketed by the Unichema company under the name STEARATE PEG 400);

PEG 8 stearate/cholesterol/phytanetriol/sodium acylglutamate, especially with a weight ratio of 47.5/20/27.5/5;

Hydrogenated lecithin/phytosterol polyoxyethylenated with 5 ethylene oxide units, especially in a weight ratio of 60/40;

Methyl glucose distearate polyoxyethylenated with 20 ethylene oxide units/cholesterol/sodium acylglutamate, especially in a weight ratio of 45/45/10 (the distearate being, for example, sold under the name GLUCAM E 9 20 distearate by Amerchol);

A/cholesterol/dicetyl phosphate especially with a weight ratio of 47.5/47.5/5 (where A is a triglyceryl cetyl ether marketed by the Chimex company under the name CHIMEXANE NL);

Diglyceryl distearate (for example that sold by Nihon under the name EMALEX DS G2)/cholesterol/sodium acylglutamate, in a weight ratio of 45/45/10;

Sucrose mono- and distearate (for example that sold by Grillo under the name GRILLOTEN PSE 141 G)/cholesterol/sodium acylglutamate, especially in a weight ratio of 45/45/10;

Tetraglyceryl tristearate (for example that sold by Nikkol under the name TETRAGLYN 3S)/cholesterol/sodium acylglutamate, especially in a weight ratio of 45/45/10.

The vesicles obtained from the following lipids may be mentioned an examples of vesicles of the second category (delivering the active substance into the surface layers of the skin):

sunflower lecithin;

NATIPIDE II (soya lecithin/ethanol/water in a weight ratio of 20/16/64, marketed by Nattermann);

C (soya lecithin/cholesterol/propylene glycol in a weight ratio of 60/20/20, marketed by Nattermann under the name NAT 50 PG);

D/dimyristyl phosphate especially in a weight ratio of 95/5 (where D is a lauryl polyglyceryl-6-cetearyl glycol ether marketed by Chimex under the name CHIMEXANE NS).

Table I below gives, for some vesicles obtained from the above lipids, the diffusion constant D of ASL in the stratum corneum and in the epidermis/dermis, as well as the glucose encapsulation ratio and the phase transition temperature of the main lipid constituting the membrane. The diffusion constant was measured for an encapsulated ASL concentration of 0.35% by weight based on the total weight of the composition.

TABLE I

| Ref. | LIPID SYSTEMS | Proportions % by weight (mg) | Diffusion coefficient D in $10^{-7}$ cm$^2$ s$^{-1}$ in the stratum corneum | Diffusion coefficient D in $10^{-7}$ cm$^2$ s$^{-1}$ in the epidermis/dermis | Degree of encapsulation of glucose in μl/mg $T_o$ | Degree of encapsulation of glucose in μl/mg $T_{24h}$ | Phase transition temperature in °C. |
|---|---|---|---|---|---|---|---|
| | 1st type = deep down | | | | | | |
| 1 | A/cholesterol/casein lipoamino acid | 45/45/10 (67.5/67.5/15) | 42 | 5 | 7.5 | 6.8 | 50 |
| 2 | B/cholesterol/dicetyl phosphate | 60/35/5 (90/52.5/7.5) | 58 | 2 | 11.1 | 11.1 | 54 |
| 3 | Span 40/cholesterol/ sodium acylglutamate | 47.5/47.5/5 (71.25/71.25/7.5) | 42 | 2 | 13.8 | 13.8 | 50 |
| 4 | PEG 8 stearate/ cholesterol/sodium acylglutamate | 47.5/47.5/5 (71.25/71.25/7.5) | 42 | 2 | 14.4 | 14.4 | 55 |
| 5 | PEG 8 stearate/ cholesterol/phytanetriol/ sodium acylglutamate | 47.5/20/27.5/5 (71.25/30/41.25/7.5) | 8.3 | 2.5 | 4.1 | 3.0 | 55 |
| 6 | Hydrogenated lecithin/ polyoxyethylenated phytosterol | 60/40 (90/60) | 8 | 2 | 6.0 | 4.8 | 80 |
| | 2nd type = surface | | | | | | |
| 7 | Sunflower lecithin | 100 (150) | 0.3 | 0.2 | 1.6 | 0 | <0 |
| 8 | Natipide II (soya lecithin/ethanol/water) | 20/16/64 (30/24/96) | 0.4 | 0.2 | 0.4 | 0 | <0 |
| 9 | C (soya lecithin/ sterols/propylene glycol) | 60/20/20 (90/30/30) | 0.25 | 0.1 | 1.8 | 0 | <0 |
| 10 | D/dimyristyl phosphate | 95/5 (142.5/7.5) | 0.3 | 0.2 | 2.0 | 0 | 14 |

The measurement of the diffusion constant D is performed by a combination of two methods employing a paramagnetic probe, ASL: on the one hand, one-dimensional and periodic electron paramagnetic resonance (EPR) and, on the other hand, kinetic EPR imagery. These two methods are described in the following papers: "Evaluation of liposomes as drug carriers into the skin by one-dimensional EPR imaging" by V. Gabrijelcic et al., International Journal of Phamaceutics, 62 (1990) p. 75–79, Elsevier, and "Liposome entrapped molecules penetration into the skin measured by nitroxide reduction kinetic imaging" by V. Gabrijelcic et al., Periodicum Biologorum, vol. 93, No. 2, p. 245–246 (1991).

The measurement of the encapsulation ratio is performed as described in "Liposomes, a practical approach" by R. R. C. New, IRL Press (1990), p. 125–136, and that of the phase transition temperature as described above.

The compositions which are the subject of the present invention find their application in a large number of cosmetic or dermatological treatments of the skin, including the scalp, such as, for example: hydration, nutrition, protection, firming-up, anti-aging, anti-wrinkle, slimming, depigmentation, anti-acne and the treatments of mycoses, of dermatitis and of psoriasis.

Thus, another subject of the invention is a use of the composition defined above for the cosmetic treatment of the skin, of the face and/or of the body and for the preparation of an ointment intended for the treatment of skin diseases. A further subject of the invention is a process for cosmetic treatment of the skin, consisting in applying the above composition to the skin.

The active substances encapsulated in the vesicles of first and second types, of course, on the intended application.

A number of active substances are advantageously employed simultaneously in each type of vesicle which have the same function and/or which exert the same type of action on the skin, at the surface and in depth; the surface and depth active substances are therefore complementary.

In particular, the active substances of the first and second type of vesicle are either anti-aging active substances or anti-wrinkle active substances or hydrating or moisturizing or slimming active substances, or depigmenting active substances or substances active against free radicals (radical oxygen species) or anti-irritation active substances or nutrient active substances or protective active substances or restructurizing active substances or firming-up active substances or anti-acne active substances or exfoliating active substances, or emollient active substances or else active substances treating skin diseases such as mycoses, dermatitis, psoriasis and the like.

By way of example, in the case of hydration, surface vesicles are used in combination with one or a number of moisturizers (or hydrating agents) such as glycerine or urea and the depth vesicles in combination with one or a number of precursor agents for the biosynthesis of structural proteins, such as hydroxyproline, collagen peptides and the like.

In the case of slimming, at least one keratolytic agent or an alpha-hydroxyacid such as salicylic acid or 5-n-octanoyl-salicylic acid encapsulated in the surface vesicles is used for example in combination with at least one liporegulating agent such as caffeine, encapsulated in the depth vesicles.

In the case of depigmentation, at least one keratolytic agent encapsulated in the surface vesicles is combined, for example, with at least one depigmenting agent such as especially a tyrosinase inhibitor (kosic acid), encapsulated in the depth vesicles.

In the case where a protection is intended against damage by radical species or singlet oxygen, it is possible, for example, to use an agent against ROO· radicals (vitamin E) or against singlet oxygen for the surface treatment in combination with an agent against $O_2^-$ free radicals (superoxide dismutase) and against OH· radicals (sugar, caffeine) for the depth treatment.

Similarly, in the case of an anti-aging action, moisturizers (sodium lactate), sunscreens, alpha-hydroxyacids (fruit acids) or surface-restructuring agents, encapsulated in surface vesicles, may be used in combination with peptides (especially soya peptide extracts), enzymes for repairing the DNA, vascular protective agents or phospholipids extracted from the octopus, which are rich in oligoelements and in C20:4, 20:5, 22:4, 22:5 and 22:6 polyunsaturated fatty acids, encapsulated in depth vesicles.

If nutrition of the skin is intended, it is possible, for example, to use at least one active substance such as sugars or fatty acids for a surface action in combination with at least one active substance such as especially vitamins and amino acids for an action in depth.

If the treatment of mycoses is envisaged, it is possible to use active substances for acting at the surface, such as, for example, exfoliants, in combination with anti-mycotic agents for acting in depth. The active substances may represent from 0.02 to 5% of the total weight of the composition. The compositions according to the invention may introduce all the galenic forms normally employed for a topical application, such as aqueous gels, emulsions, lotions, ointments, serums and more particularly oil droplets dispersed by the vesicles, as described in French Patents FR-A-2,485,921 and FR-A-2,490,504.

In a known manner, in addition to the vesicles in the compositions of the invention it is possible to find a vegetable, mineral, silicone or synthetic oil dispersed in an aqueous phase and also hydrophilic adjuvants such as gelling agents, stabilizers, opacifiers, lipophilic adjuvants such as perfumes, pigments and fillers, as described in the above French patents. The dispersed oil may represent from 2% to 40% by weight based on the total weight of the composition, and the adjuvants may represent, in all, from 0.1% to 10% by weight.

Another subject of the invention is the use of the composition defined above and a process for the anti-aging, anti-wrinkle, depigmenting, nutrient, slimming, hydrating and/or anti-acne treatment of the skin; this process consists in applying to the skin, locally or over the whole face and/or body, a composition as defined above.

The invention also relates to the use of this composition for the preparation of an ointment intended for the treatments of skin diseases, such as the treatments of the skin against mycosis, dermatitis and psoriasis.

The total weight of vesicle contained in the composition is preferably from 1 to 90 wt. %, more preferably from 5 to 70 wt. %, most preferably from 5 to 20 wt. % based on the total weight of the composition.

The ratio of the amount of vesicles of the first dispersion type which are capable of penetrating into the deep layers to the second dispersion type which are capable of penetrating into the surface layers is preferably from 1:9 to 9:1, more preferably from 3:7 to 7:3, most preferably from 4:6 to 6:4.

Within the context of the following examples the term qs 100 g is an amount needed to bring the total amount of the composition to 100 g.

Other characteristics and advantages of the invention will emerge better from the description which follows, given by way of illustration and without any limitation being implied.

A) Preparation of lipid vesicles containing ASL

The lipid constituents of the wall of the vesicles are weighed and dissolved in 10 ml of methanol. The alcoholic solution is then poured into a 50 ml ground-joint round bottom flask which is then placed on a rotary evaporator so that the content is thermostatted at a temperature of 30° C. The evaporation is continued until a dry film of lipids is deposited on the walls of the flask.

3 ml of a 0.01 molar aqueous solution of ASL are then added to the flask, which is then shaken manually for approximately 10 minutes, either at ambient temperature (20° C.) in the case of the vesicles of Table I which are given references 7 to 10, or at a temperature of 50° C. in the case of the vesicles given references 1 to 6 in Table I. The mixture is then allowed to equilibrate at ambient temperature for 2 hours and the dispersion is then placed in a dialysis bag and in contact with 500 ml of distilled water. The dialysis is performed overnight. After one night the water is changed and the dialysis is continued for 4 hours longer.

A cotton thread 0.3 mm in thickness is then soaked in the vesicle dispersion and then placed in contact with a skin section originating from a porcine ear freshly recovered from a slaughterhouse intended for the supply of food.

The ear sample is rinsed with water and cut into slices 1 mm in thickness, 5 mm in width and 10 mm in length, and is then placed in a holding cell. Measurements of diffusion of ASL in the skin are performed within the 24 hours following the sampling of skin.

B) Preparation of the cosmetic composition

1. Preparation of vesicles of first type (distributing in depth)

The (depth) vesicles are prepared by a usual method for joint melting of the chosen membrane constituents (see Table I). Thus, the membrane constituent which has the lowest melting point $T_m$ is melted; the other membrane constituents are added and then homogenization is carried out with moderate stirring and, finally, partial hydration is carried out, the melting temperature $T_m$ defined above being maintained.

An aqueous solution of at least one active substance for the treatment in depth is added to the paste obtained. A turbine is switched on for 1 h 30 min in order to have good hydration, the temperature $T_m$ being maintained. One or a number of other active substances for the treatment in depth are added to the reaction mixture, which in homogenized and the temperature of the mixture is lowered to ambient temperature (20° C).

2. Preparation of vesicles of second type (distributing at the surface)

An aqueous solution of one (or more) second active substance(s) for the surface treatment is introduced at ambient temperature (20° C.) and using simple stirring, into the chosen mixture of constituents which are to form the membrane of the surface vesicles (see Table 1). Surface vesicles encapsulating the second surface active substance are thus obtained.

3. Preparation of the "double liposomes" composition

The fatty phase of the composition is added to the mixture containing the depth vesicles and is dispersed with stirring (at ambient temperature). The reaction mixture obtained is then mixed with that containing the surface vesicles. Adjuvants are then optionally added, such as stabilizers, a gelling agent which may be neutralized, if need be, with a base (triethanolamine or sodium hydroxide) and perfumes and the like.

The product obtained is in the form of a soft and unctuous white cream which can be employed in the cosmetic and/or dermatological field depending on the nature of the chosen active (surface and depth) substances.

Individual examples of cosmetic composition in accordance with the invention are given below. The compositions are given in % by weight.

EXAMPLE 1: Depigmenting, double liposomes cream

| Depth vesicles: | |
|---|---|
| A/cholesterol/dicetyl phoshate in a weight ratio of 47.5/47.5/5 | 3% |
| Kojic acid (active substance) | 0.5% |
| Surface vesicles: | |
| D/dimyristyl phosphate in a weight ratio of 95/5 | 3% |
| Salicylic acid (active substance) | 0.3% |
| fatty phase: | |
| Vegetable or mineral oils | 10% |
| Silicone oil | 5% |
| Caffeic acid (active substance) | 0.7% |
| aqueous phase: | |
| Glycerol | 3% |
| Carboxyvinyl polymer (gelling agent) | 0.4% |
| Triethanolamine | q.s. pH = 6 |
| Demineralized water | q.s. 100% |

EXAMPLE 2: Depigmenting, double liposomes cream

This cream differs from that of Example 1 in the use of 5-n-octanoylsalicylic acid instead of salicylic acid as the active agent in the surface vesicle.

EXAMPLE 3: Anti-wrinkle, double liposomes cream

| Depth vesicles: | |
|---|---|
| PEG 8 stearate/cholesterol/sodium acylglutamate in a weight ratio of 47.5/47.5/5 | 3% |
| Soluble collagen (active substance) | 1% |
| Soya hydrolysed protein (active substance) | 0.1% |
| Surface vesicles: | |
| NAPITIDE II marketed by the Natterman company | 3% |
| Tocopherol acetate (active substance) | 0.5% |
| Glycerine (active substance) | 4.5% |
| Sodium lactate (active substance) | 0.35% |
| Fatty phase: | |
| Vegetable oils | 13% |
| Karite butter | 4% |
| Cyclomethicone | 4.% |
| Aqueous phase: | |
| Stabilizer | 1.3% |
| Perfume | 0.4% |
| Carboxyvinyl polymer (gelling agent) | 0.4% |
| Sodium hydroxide | q.s. pH = 6 |
| Water | q.s. 100% |

Obviously, numerous modifications and variations of the present invention are possible in light of the above teachings. It is therefore to be understood that within the scope of the appended claims, the invention may be practiced otherwise than as specifically described herein.

This application is based on French Patent Application 93/15863, filed with the French Patent Office on Dec. 30, 1993, the entire contents of which are hereby incorporated by reference.

What is claimed as new and desired to be secured by Letters Patent of the United States is:

1. A cosmetic or dermatological composition for the simultaneous treatment of the layers of the stratum corneum and deep layers of the skin comprising a dispersion mixture of:

i) a first dispersion of lipid vesicles capable of entering said deep layers of the skin and containing at least one active substance capable of treating said deep layers; and ii) a second dispersion of lipid vesicles capable of entering said layers of the stratum corneum of the skin and containing at least one active substance capable of treating these layers of the stratum corneum, wherein when said active substance contained in said first dispersion and said active substance contained in said second dispersion provide different effects, a) said vesicles of said first dispersion do not contain hydrogenated egg lecithin, cholesterol and dicetyl phosphate when said vesicles of said second dispersion contain soya lecithin, cholesterol and dicetyl phosphate, or b) said vesicles of said first dispersion do not contain diglycerol oleate, cholesterol and dicetyl phosphate when said vesicles of the second dispersion contain triglyceryl cetyl ether, cholesterol and dicetyl phosphate, and wherein said vesicles of said first dispersion ensure a distribution of N-(1-oxyl-2,2,6,6-tetramethyl-4-piperidyl)-N-dimethyl-N-hydroxyetbylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

2. The composition of claim 1, wherein said vesicles of said first dispersion are in a fluid state at ambient temperature and said vesicles of said second dispersion are in a gelled state at ambient temperature.

3. The composition of claim 1, wherein said vesicles of said first dispersion ensure an encapsulation potential of glucose for at least 24 hours and said vesicles of said second dispersion ensure an encapsulation potential of glucose for less than 24 hours.

4. The composition of claim 1, wherein said vesicles of said first dispersion are made up of lipids comprising at least one linear and saturated fatty chain containing from 16 to 30 carbon atoms.

5. The composition of claim 1, wherein said vesicles of said first dispersion are made up of at least one lipid selected from the group consisting of hydrogenated natural phospholipids, saturated synthetic phospholipids, polyol alkyl ethers containing at least one fatty linear chain, polyol alkyl esters containing at least one fatty chain, and a mixture thereof.

6. The composition of claim 1, wherein said vesicles of said first dispersion are made up of at least one lipid selected from the group consisting of:

1) triglyceryl cetyl ether, cholesterol, and casein lipoamino acid;

2) a mixture of triglyceryl mono-, di- and tricetyl ether, cholesterol, and dicetyl phosphate;

3) triglyceryl cetyl ether, cholesterol, and dicetyl phosphate;

4) sorbitan palmitate cholesterol, and sodium acylglutamate;

5) PEG 8 stearate, cholesterol, and sodium acylglutamate;

6) diglyceryl distearate, cholesterol, and sodium acylglutamate;

7) sucrose mono- and distearate, cholesterol, and sodium acylglutamate;

8) PEG 8 stearate, cholesterol, phytanetriol, and sodium acylglutamate;

9) methyl glucose distearate polyoxyethylenated with 20 moles of ethylene oxide, cholesterol, and sodium acylglutamate;

10) hydrogenated lecithin, and polyoxyethylenated phytosterol; and 11) tetraglyceryl tristearate, cholesterol, and sodium acylglutamate.

7. The composition of claim 1, wherein said vesicles of said second dispersion are made up of lipids selected from the group consisting of natural ionic phospholipids containing unsaturated fatty chains containing from 16 to 30 carbon atoms, polyol alkyl ethers or alkyl esters comprising one or more fatty chains per molecule, including at least one fatty chain of length shorter than 16 carbon atoms.

8. The composition of claim 1 wherein said vesicles of said second dispersion are made up of at least one lipid selected from the group consisting of:

1) sunflower lecithin;

2) soya lecithin, ethanol, and water;

3) soya lecithin, cholesterol, and propylene glycol;

4) polyglyceryl-6-cetearyl glycol lauryl ether and dimyristyl phosphate.

9. The composition of claim 16, wherein said active substances of said first and said second dispersion are the same.

10. The composition of claim 1, further comprising an oily phase dispersed in an aqueous phase.

11. The composition of claim 1, further comprising a hydrophilic adjuvants.

12. The composition of claim 1, wherein said vesicles of said first dispersion, those of said second dispersion or both contain -N-(1-oxyl-2,2,6,6-tetramethyl-4-piperidyl)-N-dimethyl-N-hydroxyethylammonium iodide.

13. An ointment for the treatment of a skin disease comprising the composition of claim 1.

14. The ointment of claim 13, wherein said active substance is effective for treatment of a skin disease selected from the group consisting of mycosis, dermatitis and psoriasis.

15. A process for cosmetic and dermatological treatment of skin, comprising applying to the skin of a patient in need thereof, an effective amount of a composition comprising a dispersion mixture of:

i) a first dispersion of lipid vesicles capable of entering the deep layers of said skin and containing at least one active substance capable of treating said deep layers; and ii) a second dispersion of lipid vesicles capable of entering the layers of the stratum corneum of the skin and containing at least one active substance capable of treating said layers, wherein when said active substance contained in said first dispersion and said active substance contained in said second dispersion provide different effects, a) said vesicles of said first dispersion do not contain hydrogenated egg lecithin, cholesterol and dicetyl phosphate when said vesicles of said second dispersion contain soya lecithin, cholesterol and dicetyl phosphate, or b) said vesicles of said first dispersion do not contain diglycerol oleate, cholesterol and dicetyl phosphate when said vesicles of the second dispersion contain triglyceryl cetyl ether, cholesterol and dicetyl phosphate, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

16. A cosmetic or dermatological composition for the simultaneous treatment of the layers of the stratum corneum and deep layers of the skin comprising a dispersion mixture of:

i) a first dispersion of lipid vesicles capable of entering said deep layers of the skin and containing at least one active substance capable of treating said deep layers; and ii) a second dispersion of lipid vesicles capable of entering said layers of the stratum corneum of the skin and containing at least one active substance capable of treating these layers of the stratum corneum, wherein when said active substance contained in said first dispersion and said active substance contained in said second dispersion provide the same function or the same effect, a) said vesicles of said first dispersion do not contain hydrogenated egg lecithin, cholesterol and dicetyl phosphate when said vesicles of said second dispersion contain soya lecithin, cholesterol and dicetyl phosphate, or b) said vesicles of said first dispersion do not contain diglycerol oleate, cholesterol and dicetyl phosphate when said vesicles of the second dispersion contain triglyceryl cetyl ether, cholesterol and dicetyl phosphate, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

\* \* \* \* \*